United States Patent
Woelfert et al.

(10) Patent No.: US 7,084,297 B2
(45) Date of Patent: Aug. 1, 2006

(54) PRODUCTION OF ISOCYANATES IN THE GASEOUS PHASE

(75) Inventors: Andreas Woelfert, Bad Rappenau (DE); Christian Mueller, Mannheim (DE); Eckhard Stroefer, Mannheim (DE); Joachim Pfeffinger, Ludwigshafen (DE); Markus Weber, Ludwigshafen (DE); Carsten Knoesche, Niederkirchen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 153 days.

(21) Appl. No.: 10/495,757

(22) PCT Filed: Nov. 19, 2002

(86) PCT No.: PCT/EP02/12930

§ 371 (c)(1), (2), (4) Date: May 27, 2004

(87) PCT Pub. No.: WO03/045900

PCT Pub. Date: Jun. 5, 2003

(65) Prior Publication Data

US 2005/0070734 A1    Mar. 31, 2005

(30) Foreign Application Priority Data

Nov. 28, 2001    (DE) ................ 101 58 160

(51) Int. Cl.
*C07C 263/00* (2006.01)
(52) U.S. Cl. ................................. 560/347
(58) Field of Classification Search .............. None
See application file for complete search history.

(56) References Cited

U.S. PATENT DOCUMENTS 6,225,497 B1 * 5/2001 Becker et al. ............ 560/347
6,264,900 B1 * 7/2001 Schubert et al. .......... 422/224

FOREIGN PATENT DOCUMENTS

| EP | 0 289 840 | 11/1988 |
|----|-----------|---------|
| EP | 0 570 799 | 11/1993 |
| EP | 0 593 334 | 4/1994  |
| EP | 0 699 657 | 3/1996  |
| EP | 0 749 958 | 12/1996 |
| EP | 0 928 785 | 7/1999  |

* cited by examiner

*Primary Examiner*—Paul A. Zucker
(74) *Attorney, Agent, or Firm*—Oblon, Spivak, McClelland, Maier & Neustadt, P.C.

(57) ABSTRACT

The invention relates to a method for producing isocyanates by reacting primary amines with phosgene in the gaseous phase. Said method is characterized in that the reaction of amine and phosgene occurs in a reaction channel, the internal dimensions of which have a width/height ratio of at least 2/1.

22 Claims, 3 Drawing Sheets

PRODUCTION OF ISOCYANATES IN THE GASEOUS PHASE

The present invention relates to a process for the preparation of isocyanates by reacting primary amines with phosgene in the gas phase, wherein the reaction of amine and phosgene is carried out in a reaction channel, preferably a plate reactor, the internal dimensions of the reaction channel having a width-to-height ratio of at least 2:1.

Various processes for the preparation of isocyanates by reacting amines with phosgene in the gas phase are known from the prior art. EP-A-593 334 describes a process for the preparation of aromatic diisocyanates in the gas phase, wherein the reaction of the diamine with phosgene takes place in a tubular reactor without moving parts and with a narrowing of the walls along the longitudinal axis of the tubular reactor. However, the process is problematic since the mixing of the starting material streams by means of a narrowing of the tube wall alone functions poorly in comparison with the use of a correct mixing element. Poor mixing usually leads to the formation of an undesirably large amount of solid.

EP-A-699 657 describes a process for the preparation of aromatic diisocyanates in the gas phase, wherein the reaction of the associated diamine with the phosgene takes place in a two-zone reactor, where the first zone, which accounts for from 20 to 80% of the total reactor volume, is ideally mixed and the second zone, which accounts for from 80 to 20% of the total reactor volume, can be characterized by plug flow. However, because at least 20% of the reaction volume are ideally back-mixed, a nonuniform residence time distribution results and may lead to the formation of an undesirably large amount of solid.

EP-A-289 840 describes the preparation of diisocyanates by gas-phase phosgenation, the preparation taking place, according to the invention, in a turbulent flow at from 200 to 600° C. in a cylindrical space without moving parts. By dispensing with moving parts, the danger of phosgene emergence is reduced. By means of the turbulent flow in the cylindrical space (tube), apart from fluid elements in the vicinity of the wall, a relatively good uniform flow distribution in the tube and hence a relatively narrow residence time distribution are achieved, which, as described in EP-A-570 799, can lead to a reduction in the formation of solid.

EP-A-570 799 relates to a process for the preparation of aromatic diisocyanates in the gas phase, wherein the reaction of the associated diamine with the phosgene is carried out in a tubular reactor above the boiling point of the diamine within an average contact time of from 0.5 to 5 seconds. As described in the publication, reaction times which are too long as well as those which are too short lead to undesired solid formation. A process in which the average deviation from the average contact time is less than 6% is therefore disclosed. This contact time is maintained by carrying out the reaction in a tube flow which is characterized either by a Reynolds number above 4 000 or a Bodenstein number above 100.

EP-A-749 958 describes a process for the preparation of triisocyanates by gas-phase phosgenation of (cyclo)aliphatic triamines having three primary amino groups, wherein the triamine and the phosgene are reacted continuously with one another in a cylindrical reaction space heated to from 200 to 600° C. at a flow rate of at least 3 m/s.

EP-A-928785 describes the use of microstructure mixers for the phosgenation of amines in the gas phase. The disadvantage of the use of micro mixers is that even very small amounts of solid, the formation of which cannot be completely ruled out in the synthesis of the isocyanates, can lead to blockage of the mixer, reducing the time for which the phosgenation plant is available.

The known gas-phase phosgenation process which uses a cylindrical reaction space offers two possibilities for the technical realization of the preparation of isocyanates on an industrial scale. Firstly, the reaction can be carried out in a single tube zone whose diameter has to be adapted to the production capacity of the plant. For very large production plants, this concept has the disadvantage that accurate heating of the reaction streams (phosgene and amine) in the core of the flow can no longer be realized by heating the wall of the tube. However, local temperature inhomogeneities can lead to product decomposition in the case of an excessively high temperature or to insufficient conversion of the starting materials into the desired isocyanate in the case of an excessively low temperature.

The second possibility for the technical realization comprises dividing the reacting mixture into individual part-streams, which are then passed parallel through smaller, individual tubes which can be better heated owing to their smaller diameter. The disadvantage of this process variant is that it is relatively susceptible to blockage unless the volume flow for each individual tube is controlled. If, for example, deposits occur at a point in one of the tubes, the pressure drop of the flow through this tube is greater. The reaction gas therefore automatically deviates to a greater extent to the other tubes.

The tube containing the deposits has a smaller flow. If, however, the flow in the tube which is beginning to be blocked is smaller, the flow in this tube has a longer residence time which, as explained in EP 570 799, leads to an increase in the formation of solid. Moreover, any solids can settle out from a slow flow substantially more easily on the tube wall, which accelerates the blockage.

In summary, it may be said that, in the industrial gas-phase phosgenation, the use of a large tube has the problem of heating of the entire flow and the use of much smaller tubes gives rise to the danger of nonuniform flow through said tubes. Both problems lead to nonuniform progress of the reaction and hence to solids, reducing the operability of the plant.

It is an object of the present invention to provide a process for the preparation of isocyanates by phosgenation in the gas phase, both a large heat exchange surface and, in spite of incompletely preventable solid formation, a very long operating time of the production plant, in particular of an industrial production plant, being achieved.

We have found that this object is achieved and that, surprisingly, the continuous phosgenation of amines in the gas phase can be carried out advantageously, i.e. for example with a substantially larger number of operating hours of the production plant, if the reaction is carried out in a noncylindrical reaction channel, preferably a plate reactor, which preferably has a height which permits advantageous heating of the reactants and which has a width which is at least two times the height.

The present invention therefore relates to a process for the preparation of isocyanates by reacting primary amines with phosgene in the gas phase, wherein the reaction of amine and phosgene is carried out in a reaction channel, the internal dimensions of the reaction channel having a width-to-height ratio of at least 2:1.

The present invention furthermore relates to the use of a plate reactor, the internal dimensions of the plate reactor having a width-to-height ratio of at least 2:1, for the preparation of isocyanates by reacting primary amines with phosgene in the gas phase.

Finally, the present invention relates to the use of a reactor lock, containing at least two of the plate reactors described above, for the preparation of isocyanates by reacting primary amines with phosgene in the gas phase.

I: Amine vessel;
II: Phosgene vessel;
III: Mixing unit.
IV: Reaction channel;
V: Working-up stage;
VI: Purification stage.
1: Solvent feed;
2: Amine feed;
3: Insert element feed;
4: Phosgene feed;
5: Discharge of hydrogen chloride, phosgene and/or inert medium;
6: Solvent discharge.
7: Isocyanate discharge.

Figure 3:
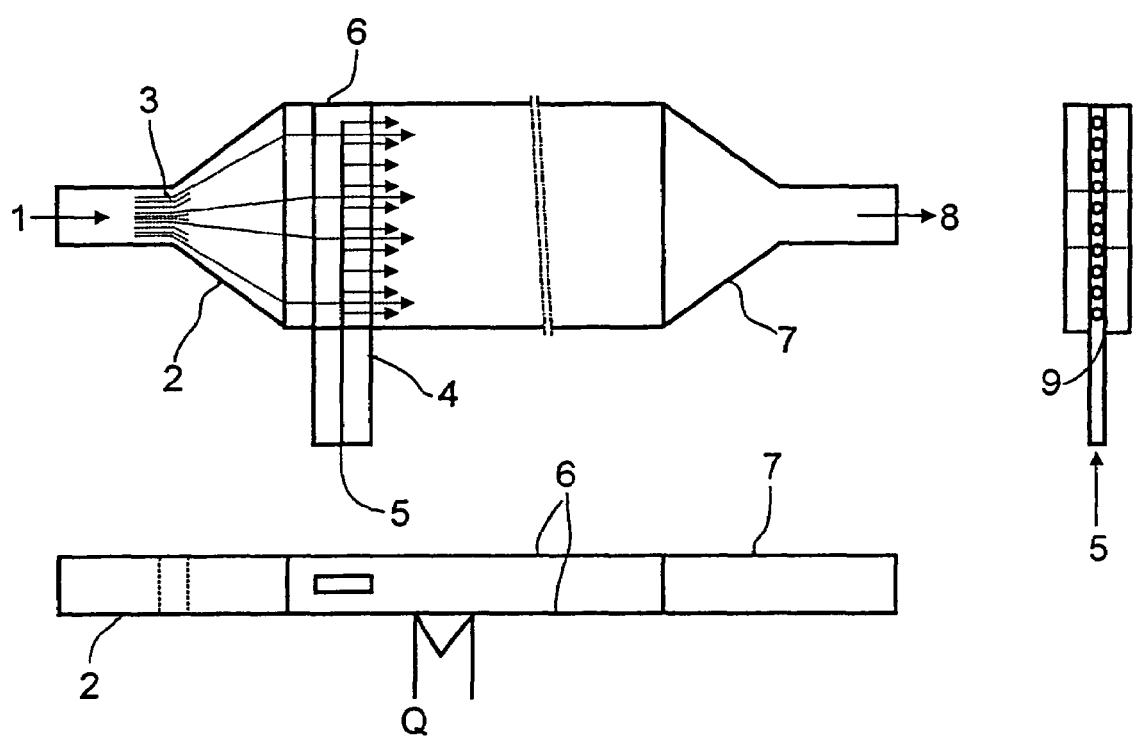

FIG. 3 shows one embodiment of a reaction channel. The reference characters identify the following elements:

1: Feed of phosgene stream
2: Distributing element;
3: Deflecting elements;
4: Distributor channel without outlet orifices for amine;
5: Amine feed;
6: Plate reactor;
7: Collecting element;
8: Outlet channel.
9: Outlet orifice for amine.

The reaction channel used in the present invention generally consists of a material which is substantially inert to the phosgenation reaction. Furthermore, it should generally withstand pressures of up to 10, preferably up to 20, bar. Suitable materials are, for example, metals, such as steel, silver or copper, glass, ceramic or homogeneous or heterogeneous mixtures thereof. Steel reactors are preferably used.

The reaction channel used is preferably substantially right parallelepiped. The reaction channel used has a width-to-height ratio of at least 2:1, preferably at least 3:1, particularly preferably at least 5:1, in particular at least 10:1. The upper limit of the width-to-height ratio depends on the desired capacity of the reaction channel and is in principle not limited. Reaction channels having a width-to-height ratio of not more than 5 000:1, preferably 1 000:1, have proven technically expedient.

The height of the reaction channel is generally not limited. Thus, it is possible, for example, to carry out the reaction in a high reaction channel having a height of, for example, 40 cm. However, if better heat exchange with the reactor walls is to be effected, the reaction can be carried out in reaction channels having a small height, for example only a few centimeters or millimeters.

In general, the reaction channel has a height of from 1 millimeter to 50 centimeters, preferably from 2 millimeters to 20 centimeters, particularly preferably from 3 millimeters to 3 centimeters.

The length of the reaction channel is dependent on the desired conversion in the reaction and is in general ten, preferably twenty, in particular fifty, times the height of the reaction channel. The length of the reactor preferably does not exceed 10 000, particularly preferably does not exceed 5 000, in particular does not exceed 4 000, times the height of the reaction channel.

In a preferred embodiment, the length of the reaction channel is at least 1 meter, usually from 2 to 50, preferably from 5 to 25, particularly preferably from 10 to 20, meters.

Figure 1:
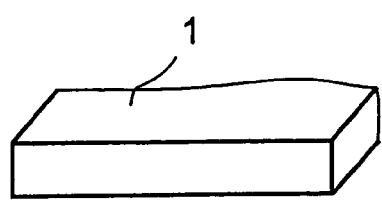
FIG. 1 shows different possible embodiments of the reaction channel. These are depicted by diagrams 1 through 8 in FIG. 1.
Figure 1:
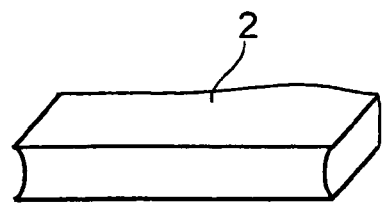
Figure 1:
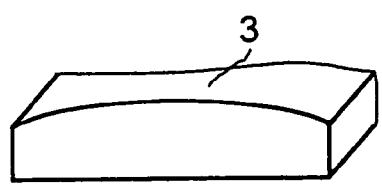
Figure 1:
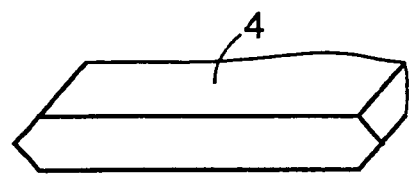
Figure 1:
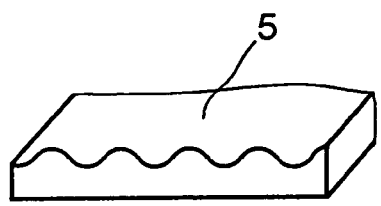
Figure 1:
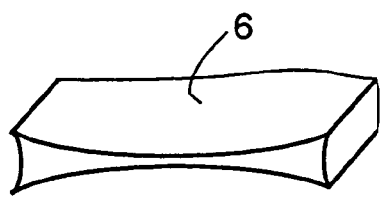
Figure 1:
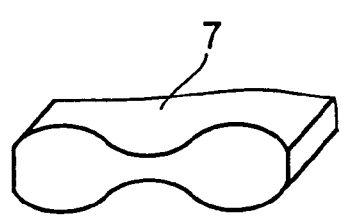
Figure 1:
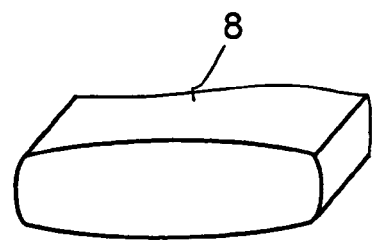

The reaction channel used is preferably substantially right parallelepiped. Depending on the technical design, however, it may have rounded corners and/or edges. The surfaces forming the right parallelepiped may likewise be curved instead of planar. If the height, width or length is not the same in all parts of the right parallelepiped, those values for the internal dimensions of the reaction channel which are disclosed in the description and in the claims relate to the average height, average width or average length. Possible embodiments of the reaction channel are shown in diagrams 1 to 8 in FIG. 1.

The walls of the reaction channel may be smooth or profiled. Examples of suitable profiles are grooves and waves.

The reaction channel used in the present invention is preferably a plate reactor. This is preferably composed of plate-like layers. Rectangular, plate-like layers are particularly preferably used. In general, the plate reactor may be composed of four rectangular, plate-like materials so that the plate reactor preferably has the shape of a right parallelepiped. The edges of such a right parallelepiped may have an angle of about 90° but they can on the other hand also be rounded.

It is also possible to assemble the plate reactor from two plate-like layers having at least one edge bent at about 90°, so that a right parallelepiped reaction channel is formed.

In a preferred embodiment, the reaction channel contains a distributing element at the inlet orifice, the distributing element containing suitable deflecting elements which distribute the gas stream very homogeneously substantially over the total width of the reaction channel. Said deflecting elements may consist, for example, of curved metal sheets.

The reaction components amine and phosgene can be mixed before or in the reaction channel. Thus, it is possible for a mixing unit, for example a nozzle, to be installed upstream of the reaction channel, with the result that a mixed gas stream containing phosgene and amine enters the reaction channel.

In a preferred embodiment, the phosgene stream is first very homogeneously distributed over the total width of the reaction channel by means of a distributing element. The amine stream is fed in at the start of the reaction channel, where a distributor channel having holes or mixing nozzles is introduced into the reaction channel, this distributor channel preferably extending over the total width of the reaction channel. From the holes or mixing nozzles, the amine, which may be mixed with an inert medium, is fed to the phosgene stream.

The inert medium is a medium which is present in gaseous form at the reaction temperature and does not react with the starting materials. For example, nitrogen, noble gases, such as helium or argon, or aromatics, such as chlorobenzene, dichlorobenzene or xylene, may be used. Nitrogen is preferably used as the inert medium.

Primary amines which can be converted into the gas phase, preferably without decomposition, can be used for the novel process. Amines, in particular diamines, based on aliphatic or cycloaliphatic hydrocarbons of 1 to 15 carbon atoms are particularly suitable here. Examples of these are 1,6-diaminohexane, 1-amino-3,3,5-trimethyl-5-aminomethylcyclohexane (IPDA) and 4,4'-diaminodicyclohexylmethane. 1,6-Diaminohexane (HDA) is preferably used.

Aromatic amines which can be converted into the gas phase preferably without decomposition can also be used for the novel process. Examples of preferred aromatic amines are toluenediamine (TDA), as 2,4- or 2,6-isomer or as a mixture thereof, diaminobenzene, naphthalenediamine (NDA) and 2,4'- or 4,4'-methylene(diphenylamine) (MDA) or isomer mixtures thereof.

In the novel process, it is advantageous to use phosgene in excess relative to amino groups. Usually, a molar ratio of phosgene to amino groups of from 1.1:1 to 20:1, preferably from 1.2:1 to 5:1, is present.

For carrying out the novel process, it may be advantageous to preheat the streams of the reactants prior to mixing, usually to temperatures of from 100 to 600° C., preferably from 200 to 500° C. The reaction in the reaction channel usually takes place at from 150 to 600° C., preferably from 250 to 500° C. The novel process is preferably carried out continuously.

In a preferred embodiment, the dimensions of the reaction channel and the flow rates are such that turbulent flow, i.e. flow having a Reynolds number of at least 2 300, preferably at least 2 700, is present, the Reynolds number being calculated using the hydraulic diameter of the reaction channel. Preferably, the gaseous reactants pass through the reaction channel at a flow rate of from 20 to 150, preferably from 30 to 100, meters/second.

In the novel process, average contact time is generally from 0.05 to 5 seconds, preferably from 0.06 to 1, particularly preferably from 0.1 to 0.45, second. Average contact time is understood as meaning the time span from the beginning of mixing of the starting material to washing-out of the reaction gas after leaving the reaction channel in the working-up stage. In a preferred embodiment, the flow in the novel process is characterized by a Bodenstein number of more than 10, preferably more than 100, particularly preferably more than 500.

Figure 2:
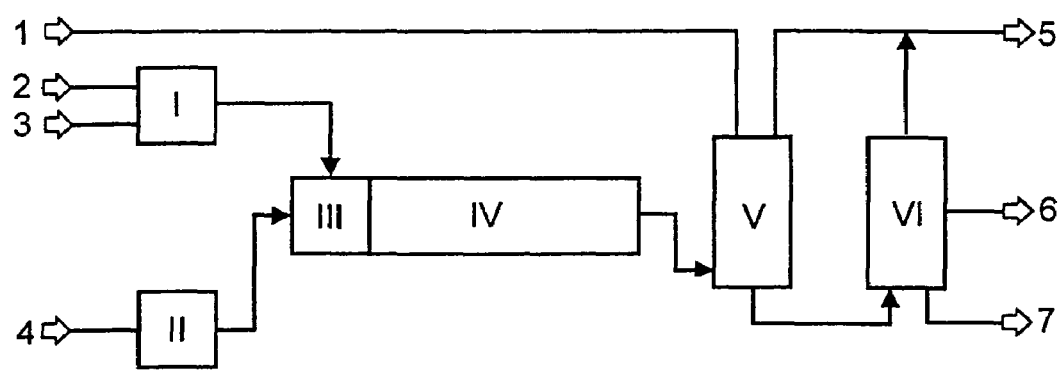
FIG. 2 schematically depicts one embodiment of the process of the invention. The reference characters identify the following elements.

A preferred embodiment of the novel process is shown schematically in FIG. 2.

In FIG. 2, the meanings are as follows:
I Amine vessel
II Phosgene vessel
III Mixing unit
IV Reaction channel
V Working-up stage
VI Purification stage
1 Solvent feed
2 Amine feed
3 Inert medium feed
4 Phosgene feed
5 Discharge of hydrogen chloride, phosgene and/or inert medium
6 Solvent discharge
7 Isocyanate discharge In the amine vessel, the amine, if required together with an inert medium as a carrier gas, for example nitrogen, is converted into the gas phase and fed into the mixing unit. Likewise, phosgene from the phosgene vessel is transferred to the mixing unit. After mixing in the mixing unit, which, for example, may consist of a nozzle or a static mixer, the gaseous mixture comprising phosgene, amine and, if required, inert medium is transferred to the reaction channel. As shown in FIG. 2, the mixing unit need not be an independent reaction stage; rather, it may be advantageous to integrate the mixing unit into the reaction channel. A preferred embodiment of an integrated unit comprising mixing unit and reaction channel is shown in FIG. 3.

After the reaction mixture has been reacted in the reaction channel, it enters the working-up stage. This is preferably a scrubbing tower, the isocyanate formed being separated from the gaseous mixture by condensation in an inert solvent, while excess phosgene, hydrogen chloride and any inert medium pass through the working-up stage in gaseous form. Suitable inert solvents are preferably aromatic hydrocarbons which are unsubstituted or substituted by halogen, for example chlorobenzene, dichlorobenzene and toluene. Particularly preferably, the temperature of the inert solvent is kept above the decomposition temperature of the carbamoyl chloride belonging to the amine.

In the subsequent purification stage, the isocyanate is separated from the solvent, preferably by distillation. Here, remaining impurities comprising hydrogen chloride, inert medium and/or phosgene can also be separated off.

FIG. 3 shows a preferred embodiment of a reaction channel. In this embodiment, the reaction channel consists of a plate reactor which contains, at the two outlet orifices, a distributing element and a collecting element.

In FIG. 3, the meanings are as follows:
1 Feed of phosgene stream
2 Distributing element
3 Deflecting elements
4 Distributor channel with outlet orifices for amine
5 Amine feed
6 Plate reactor
7 Collecting element
8 Outlet channel
9 Outlet orifices for amine The gaseous phosgene stream used is very homogeneously distributed over the total width of the plate reactor by a distributing element. Deflecting elements which, for example, may consist of angled metal sheets can be used for this purpose. The amine is added via a distributor channel, which preferably extends over the total width of the plate reactor and is preferably arranged in spatial proximity to the distributing element. The distributor channel is preferably arranged at middle height in the plate reactor and contains holes or mixing nozzles via which the amine stream is fed to the plate reactor and is thus mixed with the phosgene stream. At the other end of the plate reactor, the gas stream is preferably focused in a collecting element and then fed to the working-up stage.

The addition of the inert solvent for washing out the isocyanate can be effected in the washing tower and/or as early as in the outlet region of the plate reactor 6 and/or between plate reactor 6 and collecting element 7 and/or in the collecting element 7 and/or in the outlet channel 8. In an advantageous embodiment, the reaction gases from the reaction channel are brought into contact with the inert solvent as far as possible after the same residence time in the reaction channel. In a preferred embodiment, the inert solvent is brought into contact with the reaction gas by means of nozzles which are mounted at the abovementioned points.

In a preferred embodiment, the novel process is carried out in a reactor block, the latter containing two or more, preferably from 2 to 20, reaction channels described above, preferably plate reactors. The reaction channels may be arranged as desired within the reactor block and are preferably arranged one on top of the other. A suitable reactor block is, for example, an appropriately dimensioned tube in whose interior two or more reaction channels are arranged. The reaction of phosgene with amine consequently takes place only in the novel reaction channels and not in the reactor block. The reactor block serves merely as a sort of casing for the reaction channels.

In a particularly preferred embodiment, the reactor block contains, in addition to the reaction channels, a fluid which can flow between the individual reaction channels. This fluid serves for heat removal, i.e. for temperature regulation inside the reaction channels. Suitable fluids are substances which withstand temperatures up to about 350° C. without decomposition, for example heat transfer oils, such as Marlotherm®, or salt melts, such as sodium/potassium nitrites and/or sodium/potassium nitrates. Heat removal by evaporative cooling, for example by water, is also possible.

The examples which follow illustrate the invention.

EXAMPLE 1

Use of a Plate Reactor 40 mol/h of hexamethylenediamine and 40 mol/h of monochlorobenzene were mixed with one another, vaporized and preheated to 320° C. The resulting gas stream was mixed with 160 mol/h of gaseous phosgene, which was likewise preheated to 320° C., in a mixing nozzle apparatus consisting of a mixing chamber having two inlets opposite one another, with an inlet rate of in each case 80 m/s on the phosgene and on the hexamethylenediamine/monochlorobenzene inlet side. The gas mixture emerging from the mixing chamber was passed to a rectangular channel having a width of 8 mm, a height of 62.8 mm and a length of 20 m. The channel was heated on the two 62.8 mm wide sides to a temperature of 320° C. by means of electrical heating tapes. After emerging from the channel, the hexamethylene diisocyanate (HDI) was washed selectively out of the reaction mixture in a known manner (cf. for example U.S. Pat. No. 2,480,089) above the decomposition temperature of the associated carbamoyl chloride using monochlorobenzene at 165° C. The desired HDI was separated from the washing medium monochlorobenzene by distillation in a yield of 98.5%. By applying reduced pressure to the scrubbing tower, an absolute pressure of 350 mbar was established in the scrubbing tower and in the upstream reaction tube. Pressure measuring means were installed between the channel and the mixing apparatus and in the scrubbing tower. At the beginning of the experiment, a pressure difference of about 79 mbar resulted between the pressure measuring points between mixer and channel and at the pressure measuring point at the entrance into the scrubbing tower, corresponding roughly to the pressure drop of the flow due to friction in the tube. After an operating time of 24 hours, there was still no sign of an increase in the pressure difference, which would indicate a reduction in the free cross section due to solid formation in the tube.

COMPARATIVE EXAMPLE 2

Use of a tubular reactor consisting of 10 parallel part-tubes, the total cross-sectional area of all tubes corresponding to the cross-sectional area between the two plates.

Analogously to example 1, 40 mol/h of hexamethylenediamine and 40 mol/h of monochlorobenzene were mixed with one another, vaporized and preheated to 320° C. The resulting gas stream was mixed with 160 mol/h of gaseous phosgene, which had likewise been preheated to 320° C., in a mixing nozzle apparatus consisting of a mixing chamber having two inlets opposite one another, with an inlet rate of in each case 80 m/s on the phosgene and hexamethylenediamine/monochlorobenzene inlet side. The gas mixture emerging from the mixing chamber was distributed over 10 parallel tubes having a circular diameter of 8 mm and a length of 20 m. The tubes were heated to 320° C. by means of electrical heating tapes. After emerging from the tubes, the hexamethylene diisocyanate (HDI) was washed selectively out of the reaction mixture in a known manner (cf. for example U.S. Pat. No. 2,480,089) above the decomposition temperature of the associated carbamoyl chloride using monochlorobenzene at 165° C. The desired HDI was separated from the washing medium monochlorobenzene by distillation in a yield of 98.5%. By applying reduced pressure to the scrubbing tower, an absolute pressure of 350 mbar was established in the scrubbing tower and in the upstream reaction tubes. Pressure measuring means were installed between the tubes and the mixing apparatus and in the scrubbing tower. At the beginning of the experiment, a pressure difference of about 162 mbar resulted between the pressure measuring points between mixer and reaction tube and at the pressure measuring point at the entrance into the scrubbing tower, corresponding roughly to the pressure drop of the flow due to friction in the tube. After an operating time of 24 hours, the pressure difference in one of the tubes increased from 162 mbar to 187 mbar, indicating a reduction in the free cross section due to solid formation in the tube. The experiment was then terminated.

We claim:

1. A process for the preparation of isocyanates comprising:
   reacting at least one primary amine with phosgene in the gas phase,
   wherein the reaction of amine and phosgene is carried out in a reaction channel, the internal dimensions of the reaction channel having a width-to-height ratio of at least 2:1.

2. The process of claim 1, wherein the reaction channel is a plate reactor, the internal dimensions of the plate reactor having a width-to-height ratio of at least 2:1.

3. The process of claim 1, wherein the internal dimensions of the reaction channel have a height of from 1 millimeter to 50 centimeters.

4. The process of claim 1, wherein the length of the reaction channel is at least ten times the width of the reaction channel.

5. The process of claim 1, wherein the primary amine used is toluenediamine, 1,6-diaminohexane, 1-amino-3,3,5-trimethyl-5-aminomethylcyclohexane or 4,4'-diaminodicyclohexylmethane.

6. The process of claim 1, wherein the gaseous phosgene used is distributed over the total width of the reaction channel by a distributing element at the entrance of the reaction channel and the gaseous amine is fed to the distributed phosgene stream.

7. The process of claim 2, wherein the reaction is carried out in a reactor block containing two or more of the plate reactors.

8. The process of claim 7, wherein the reactor block contains a fluid which is suitable for temperature regulation and at least partly surrounds the plate reactors.

9. The process of claim 1, wherein the reaction channel has a width-to-height ratio of at least 3:1.

10. The process of claim 1, wherein the reaction channel has a width-to-height ratio of at least 5:1.

11. The process of claim 1, wherein the reaction channel has a width-to-height ratio of at least 10:1.

12. The process of claim 1, wherein the reaction channel has a width-to-height ratio of at least 1,000:1.

13. The process of claim 1, wherein the reaction channel has a width-to-height ratio of at least 5,000:1.

14. The process of claim 1, wherein the length of the reaction channel does not exceed 10,000 times its height.

15. The process of claim 1, wherein the length of the reaction channel does not exceed 4,000 times its height.

16. The process of claim 1, wherein the walls of the reaction channel are smooth.

17. The process of claim 1, wherein the walls of the reaction channel are profiled.

18. The process of claim 1, wherein the amine is at least one diamine based on an aliphatic or cycloaliphatic hydrocarbon having 1 to 15 carbon atoms.

19. The process of claim 1, wherein the ratio of phosgene to amino groups ranges from 1.2 to 1 to 5:1.

20. The process of claim 1, wherein the reactants are preheated to 200–500° C. prior to mixing.

21. The process of claim 1, which occurs under turbulent flow characterized by a Reynold's number of at least 2,700.

22. The process of claim 1, wherein the flow is characterized by a Bodenstein number more than 100.

* * * * *